United States Patent [19]

Roe

[11] Patent Number: 5,516,572

[45] Date of Patent: May 14, 1996

[54] LOW REWET TOPSHEET AND DISPOSABLE ABSORBENT ARTICLE

[75] Inventor: Donald C. Roe, West Chester, Ohio

[73] Assignee: The Procter & Gamble company, Cincinnati, Ohio

[21] Appl. No.: 210,525

[22] Filed: Mar. 18, 1994

[51] Int. Cl.$^6$ ........................................... B32B 3/10
[52] U.S. Cl. ........................................ 428/131; 428/137
[58] Field of Search ................................. 428/131, 137

[56] References Cited

U.S. PATENT DOCUMENTS

| | | | |
|---|---|---|---|
| 3,016,599 | 1/1962 | Perry, Jr. ................................. | 28/78 |
| 3,485,706 | 1/1968 | Evans ...................................... | 161/72 |
| 3,862,472 | 1/1975 | Norton et al. ......................... | 19/145.5 |
| 4,100,324 | 7/1978 | Anderson et al. ..................... | 428/288 |
| 4,107,364 | 8/1978 | Sisson .................................... | 428/196 |
| 4,209,563 | 6/1980 | Sisson .................................... | 428/288 |
| 4,442,062 | 4/1984 | Fujii et al. ............................. | 264/518 |
| 4,469,734 | 9/1984 | Minto et al. .......................... | 428/134 |
| 4,493,868 | 1/1985 | Meitner .................................. | 428/171 |
| 4,610,681 | 9/1986 | Strohbeen et al. .................... | 604/396 |
| 4,646,362 | 3/1987 | Heran et al. .......................... | 2/400 |
| 4,704,112 | 11/1987 | Suzuki et al. ......................... | 604/378 |
| 4,773,903 | 9/1988 | Weisman et al. ..................... | 604/368 |
| 4,808,467 | 2/1989 | Suskind et al. ....................... | 428/284 |
| 4,865,596 | 9/1989 | Weisman et al. ..................... | 604/368 |
| 4,879,170 | 11/1989 | Radwanski et al. ................... | 428/233 |
| 4,891,258 | 1/1990 | Fahrenkrug ............................. | 428/138 |
| 4,923,454 | 5/1990 | Seymour et al. ...................... | 604/368 |
| 4,931,355 | 6/1990 | Radwanski et al. ................... | 428/283 |
| 4,939,016 | 7/1990 | Radwanski et al. ................... | 428/152 |
| 4,950,531 | 8/1990 | Radwanski et al. ................... | 428/284 |
| 4,957,795 | 9/1990 | Riedel ..................................... | 428/74 |
| 4,965,122 | 10/1990 | Morman .................................. | 428/225 |
| 4,991,387 | 2/1991 | Tashiro et al. ......................... | 57/256 |
| 5,047,456 | 9/1991 | Onwumere et al. ................... | 524/13 |
| 5,098,764 | 3/1992 | Drelich et al. ......................... | 428/131 |
| 5,108,827 | 4/1992 | Gessner ................................... | 428/219 |
| 5,143,779 | 9/1992 | Newkirk et al. ....................... | 428/218 |
| 5,144,729 | 9/1992 | Austin et al. .......................... | 28/105 |
| 5,145,727 | 9/1992 | Potts et al. ............................. | 428/198 |
| 5,198,057 | 3/1993 | Newkirk et al. ....................... | 156/83 |

FOREIGN PATENT DOCUMENTS

| | | |
|---|---|---|
| 2049398 | 2/2992 | Canada ........................... A61F 13/15 |
| 0418493 | 3/1991 | European Pat. Off. . |
| 0472355A1 | 2/1992 | European Pat. Off. . |
| 0523719A1 | 7/1992 | European Pat. Off. ........ A61F 13/15 |
| 1-201566 | 1/1988 | Japan . |

OTHER PUBLICATIONS

Derwent Publications Ltd., Abstract No. 89-275290/38; (JO 1201-566-A; Asahi Chemical Ind. KK; "Bulky Spun-bond Nonwoven Fabric—Used Especially as Top Sheet For Diaper, Etc.".

*Primary Examiner*—Christopher W. Raimund
*Attorney, Agent, or Firm*—Loretta J. Henderson; Donald J. Brott; Kevin C. Johnson

[57] ABSTRACT

A disposable absorbent article contains a liquid pervious topsheet, having a basis weight ranging from 10 to 40 g/yd$^2$ and comprising a body with at least the upper portion thereof comprising nonwoven fabric prepared by forming a web comprising a homogeneous admixture of from 1 to 50% by weight of melt blown fibers and from 99 to 50% by weight of 1.2 to 5 denier staple synthetic fibers and hydroentangling the fibers to form a fabric, with or without the formation of apertures.

11 Claims, 2 Drawing Sheets

LOW REWET TOPSHEET AND DISPOSABLE ABSORBENT ARTICLE

TECHNICAL FIELD

This invention relates to a low rewet topsheet for disposable absorbent articles and to disposable absorbent articles containing low rewet topsheets.

BACKGROUND OF THE INVENTION

Apertured topsheets are considered important in disposable absorbent articles (e.g., disposable diapers, training pants, adult incontinent products or sanitary napkins) for handling runny discharges, e.g., runny bowel movements. Topsheets composed only of staple synthetic fibers, while having excellent strength and fluid handling properties, are not as soft as desired and do not always have precisely defined apertures. On the other hand, topsheets containing a layer of melt blown fibers as the top (exposed)layer, while having good softness and clean apertures, have relatively high rewet values and are sometimes prone to "linting."

European Patent Application 0418493 teaches an apertured topsheet comprising at least one layer of textile fibers and at least one layer of melt blown fibers combined to form an apertured fabric by hydroentangling, which solves the aforementioned problems to a great extent but still is somewhat deficient in rewet properties.

However, improved rewet properties and improved opacity (white appearance) of land areas, compared to what can be obtained by following European Patent Application 0418493, would be desirable.

Furthermore, there are applications where apertured topsheets are not required. In these cases, improved combination of strength, softness, rewet, and opacity properties would be desirable.

SUMMARY OF THE INVENTION

One embodiment herein is directed to a liquid pervious topsheet for a disposable absorbent article, having a basis weight ranging from 10 to 40 grams/square yard (i.e., g/yd$^2$) (12 to 48 g/m$^2$), preferably from 15 to 30 g/yd$^2$ (18 to 36 g/m$^2$), and consisting of an apertured body with at least the upper portion thereof comprising nonwoven fabric prepared by forming a web comprising a homogeneous admixture of from 1 to 50% by weight of melt blown fibers, preferably non-elastic polyester fibers, and from 99 to 50% by weight of 1.2 to 5 denier staple synthetic fibers, preferably carded fibers, preferably bicomponent fibers, and hydroentangling the fibers to form a fabric and to form effective apertures therein, preferably effective apertures having open area occupying 8 to 40%, very preferably 12 to 25%, of the exposed surface area of the fabric. Preferably the apertures are symmetrically spaced with respect to the exposed (i.e., body side) surface of the fabric. This topsheet has good strength and softness, clean apertures and improved rewet properties and improved opacity (white appearance) of land areas compared to a topsheet that can be obtained by following European Patent Application 0418493.

Another embodiment herein is directed to a disposable absorbent article comprising a liquid pervious topsheet, a liquid impervious backsheet and an absorbent core positioned between the topsheet and the backsheet, the liquid pervious topsheet having a basis weight ranging from 10 to 40 g/yd$^2$ (12 to 48 g/m$^2$), preferably from 15 to 30 g/yd$^2$ (18 to 36 g/m$^2$), and having at least the upper portion thereof comprising nonwoven fabric prepared by forming a web comprising a homogeneous admixture of from 1 to 50% by weight of melt blown fibers, preferably non-elastic polyester fibers, and from 99 to 50% by weight of 1.2 to 5 denier staple synthetic fibers, preferably carded fibers, preferably bicomponent fibers, and hydroentangling, with or without the formation of apertures as described above. Even in the case where the topsheet is non-apertured, the disposable absorbent article provides an improved combination of strength, softness, rewet and opacity properties.

The term "disposable absorbent article" is used herein to mean disposable diapers, training pants, adult incontinent products, sanitary napkins and the like. Such articles preferably contain a liquid pervious topsheet, a liquid impervious backsheet and an absorbent core positioned between the topsheet and the backsheet.

The term "topsheet" is used herein to mean the liquid pervious layer on the body side of the absorbent core in a disposable absorbent article. In a disposable diaper, it is sometimes referred to as the diaper liner. The fabric or stock from which the topsheet is fashioned is sometimes referred to as cover stock.

The "upper portion" of the topsheet is used herein to mean the portion on the body side of the topsheet when the disposable absorbent article is in use, i.e., the side opposite to that facing the absorbent core.

The term "homogeneous admixture" is used herein to mean substantially the same composition in any area of 2 square centimeters as determined by analysis of average gray levels of different regions using the image acquisition and measurement procedures described below (with respect to determining percentage open area).

The term "melt blown" is discussed in detail below.

The term "staple" is used herein to refer to fibers, that when spun, form a yarn.

The term "carded fibers" is used herein to refer to fibers obtained by disintegrating a carded fiber web, i.e., a web obtained in a process wherein a bale of staple fibers is opened, cleaned, aligned and formed into a continuous unbonded web, using a carding machine which comprises a series of rolls which are covered with card clothing (wire teeth set a foundation fabric on narrow serrated metal flutes spirally arranged about the rolls) which functions to separate and align the fibers. Optionally, melt blown fibers may be formed and introduced into the stream of staple fibers just prior to deposition on the carding rolls.

The term "hydroentangle" is discussed in detail below.

The term "effective aperture" is used herein to mean those areas on the fabric which have a gray level of 18 or less on a standard gray level scale of 0–255, under the image acquisition parameters described hereafter. The effective apertures may be through the thickness of the fabric, through a portion of the thickness of the fabric (i.e., present on a surface of the fabric), or within the body of the fabric. Typically, the effective apertures are through the thickness of the fabric. By "thickness" of the fabric is meant the dimension of the fabric which is normal to the body side surface of the fabric. In addition, an aperture may be divided into plural effective apertures by transverse fibers. The percentage of exposed surface area of a fabric occupied by open area of effective apertures is the average percentage open area determined by the following procedure using the image analysis system described below. The procedure has two principal steps: image acquisition, i.e., obtaining representative images of areas on the exposed (i.e., body side) surface of the fabric, and image measurement, i.e., measuring the percentage open area of an image. An image analysis system having a frame grabber board, microscope, camera and image analysis software is utilized. A model DT2855 frame grabber board available from Data Translation of Marlboro, Mass. is provided. A VH5900 monitor microscope, a video camera having a VH50 lens with a contact type illumination head available from the Keyence Company of Fair Lawn, N.J. is also provided and used to acquire an image to be saved to computer file. The Keyence microscope acquires the image and the frame grabber board converts the analog signal of this image into computer readable digital format. The image is saved to computer file and measured using suitable software such as the Optimas Image Analysis software, version 3.1, available from the BioScan Company of Edmonds, Wash. In order to use the Optimas Image Analysis software, the computer should have Windows software, version 3.0 or later, available from the Microsoft Corporation of Redmond, Wash. and also have a CPU at least equivalent to the Intel 80386. Any suitable desk top PC may be used, with a 486 DX33 type PC having been found to be particularly suitable. Images being saved to and recalled from file are displayed on a Sony Trinitron monitor model PVM-1343MO with a final display magnification of about 50X. The image acquisition step noted above requires 10 different regions from a sample to be tested. Each region is rectangular, measuring about 5.8 millimeters by 4.2 millimeters. The sample is placed on a black mat board to increase the contrast between the apertures and the portion of the sample which defines the apertures. The mean gray level and standard deviation of the black mat board are 16 and 4, respectively. Images are acquired with room lights off using the Keyence monitor microscope mounted on a copystand directly above the sample. The Keyence light source illuminating the sample is adjusted and monitored with the Optimas software to measure the mean gray level and standard deviation of a 0.3 density wedge on a Kodak Gray Scale available from the Eastman Kodak Company of Rochester, N.Y. The control of the Keyence light source is adjusted so that the mean gray level of the illuminated wedge is 111±1 and the standard deviation is 10±1. All images are acquired during a single time period, and the Keyence light source is monitored by measuring the mean gray level and standard deviation of the wedge throughout the image acquisition process. The image analysis software is calibrated in millimeters by a ruler image acquired from the sample images. A 3 by 3 pixel averaging filter found in the Optimas 3.1 Image menu is applied to each saved image to reduce noise. The open areas of the apertures are detected in the gray level range of 0 through 18. Individual apertures which cannot be fully viewed in the image are included in the percentage open area calculation. The percentage open area is simply the image of pixel ratios from 0 through 18 to the total number of pixels in the image. Areas having a gray level 19 or greater are not counted as open area in the open area calculation. The percentage open area for the average of 10 images for each sample is measured using the Optimas Image Analysis software. The percentage open area is defined as the ratio of the number of pixels having a gray level from 0 through 18 to the total number of pixels for the image, multiplied by 100. The percentage open area is measured for each image representing one particular region from a sample. The percentage open area from each of the 10 individual images is then averaged to yield a percentage open area for the entire sample.

The denoration of effective apertures having open area occupying a percentage of the exposed surface area of the fabric means that the determination is carried out on the exposed surface of the fabric, i.e., the surface that will face the body when a topsheet fabricated from the fabric is in use in a disposable absorbent article.

The term "rewet" is used herein to mean retransmission of liquid from the absorbent core to the body or wearer side of the topsheet when the disposable absorbent article is in use. Low rewet means low retransmission of liquid from the absorbent core to the body or wearer side of the topsheet. Rewet property of a topsheet is determined herein by the following procedure. A stack of three pieces (each 4" by 4", i.e., 10.16 cm×10.16 cm) of Ahlstrom No. 989 filter paper (Ahlstrom Filtration, P.O. Box A, Mr. Holly Springs, Pa.) is assembled to represent an absorbent core. A 5" by 5" (12.70 cm×12.70 cm) piece of the topsheet to be evaluated is placed on top of this "core stack." A "strikethrough plate" is placed on top of the piece of topsheet. The "strikethrough plate" is composed of Plexiglas and has an outlet opening at the bottom of a 1 inch (2.54 cm) diameter bore which has a center circular "hub" with a diameter of 0.64 cm with 6 symmetrically positioned "spokes" extending 0.95 cm from the "hub." Synthetic urine (Jayco SynUrine® obtainable from Jayco Pharmaceuticals Company of Camp Hill, Pa. having a pH in the range of 6.0 to 6.4 and having the formula: 2.0 grams/liter (i.e., g/l) of KCl; 2.0 g/l of $Na_2SO_4$; 0.85 g/l of $(NH_4)H_2PO_4$; 0.15 g/l $(NH_4)_2HPO_4$; 0.19 g/l of $CaCl_2$; and 0.23 g/l of $MgCl_2$; all the chemicals being reagent grade) in the amount of 5.0 g is added to the sample by introducing the synthetic urine into the bore of the "strikethrough plate," keeping the fluid in the cavity above the outlet opening in the plate during the entire fluid addition procedure. The "strikethrough plate" is then removed and slowly (over a span of about 5 seconds) an eight pound weight is placed on top of the topsheet on the "core stack." The weight is 4" by 4" (10.16 cm×10.16 cm) and has a 1" (2.54 cm) thick piece of polyurethane foam (Presto-foam #305 Natural, Presto Mfg. Co., Inc., Brooklyn, N.Y. 11211) attached at its bottom to more evenly distribute the applied pressure. The foam is covered with a piece of 1.2 mil thick polyethylene so the foam will not absorb any of the synthetic urine. Once the weight has been applied, a timer is immediately started. After exactly 180 seconds, the weight is removed and its bottom (the polyethylene) is quickly and carefully dried. Then two pieces (5" by 5", i.e., 12.70 cm×12.70 cm, squares) of pre-weighed Ahlstrom No. 632 filter paper (i.e., "pickup paper") are placed on top of the topsheet on the "core stack." The weight is slowly reapplied (over a span of at least 5 seconds). The weight is removed after 120 seconds and the "pickup paper" is reweighed. The rewet value is the net increase in weight of the two pieces of "pickup paper" in grams.

The opacity of land areas of the exposed surface of the topsheet (i.e., the surface that will face the body when the topsheet is in use in a disposable absorbent article) is measured herein in terms of gray level as specified hereinafter using the image acquisition and measurement procedures described above (with respect to determining average percentage open area).

Tensile strength is evaluated herein by breaking a one-inch (2.54 cm) by seven-inch (17.78 cm)long sample generally following ASTM D1682-64, the One-Inch Cut Strip Test.

DETAILED DESCRIPTION OF PREFERRED EMBODIMENTS

We turn now to the preparation of the nonwoven fabric from which at least the upper portion of the topsheet is constituted.

As indicated above this is carried out by forming a web comprising a homogeneous admixture of from 1 to 50% by weight of melt blown fibers and from 99 to 50% by weight of 1.2 to 5 denier staple synthetic fibers and hydroentangling the fibers.

By varying the relative proportion of melt blown fibers and staple synthetic fibers in the homogeneous admixture, a desired combination/balance of characteristics (particularly softness, appearance, resiliency, strength, strikethrough/rewet) is obtained.

Preferably the homogeneous admixture comprises 2 to 25% by weight of melt blown fibers and from 98 to 75% by weight of 1.2 to 5 denier synthetic staple fibers.

The melt blown fibers typically have a denier ranging from 0.1 to 0.5 and a length ranging from several microns (e.g., 3 microns) to 0.1 inch (0.25 cm).

The meltblown fibers can be non-elastic or elastic. Non-elastic melt blown fibers can be prepared from polyolefins such as polypropylene and polyethylene, copolymers of olefins including ethylene and propylene, polyesters such as polybutylene terephthalate and polyethylene terephthalate and polyamides such as nylon 6 and nylon 66. Elastic melt blown fibers can be prepared from various elastomeric materials including polyester elastomers, polyurethane elastomers, polyetherester elastomers, polyamide elastomers, and elastomeric A—B—A' block copolymers (e.g., as described in U.S. Pat. No. 4,323,534 and U.S. Pat. No. 4,355,425, both incorporated herein by reference). Suitable elastomers include those sold under the names Hytrel® (polyester), Estane® (polyurethane), Arnitil® (polyetherester), Pebax® (polyamide) and Kraton® (A—B—A' block copolymer). Preferred melt blown fibers are non-elastic polyester fibers, most preferably polybutylene terephthalate fibers.

The melt blown fibers are prepared by heating the selected polymeric material to form a liquid and extruding the liquified polymer through orifices in a die into a high velocity gaseous stream to attenuate and solidify the extruded material into fibers which may be collected on a screen disposed in the gaseous stream as an entangled coherent mass.

Figure 1:
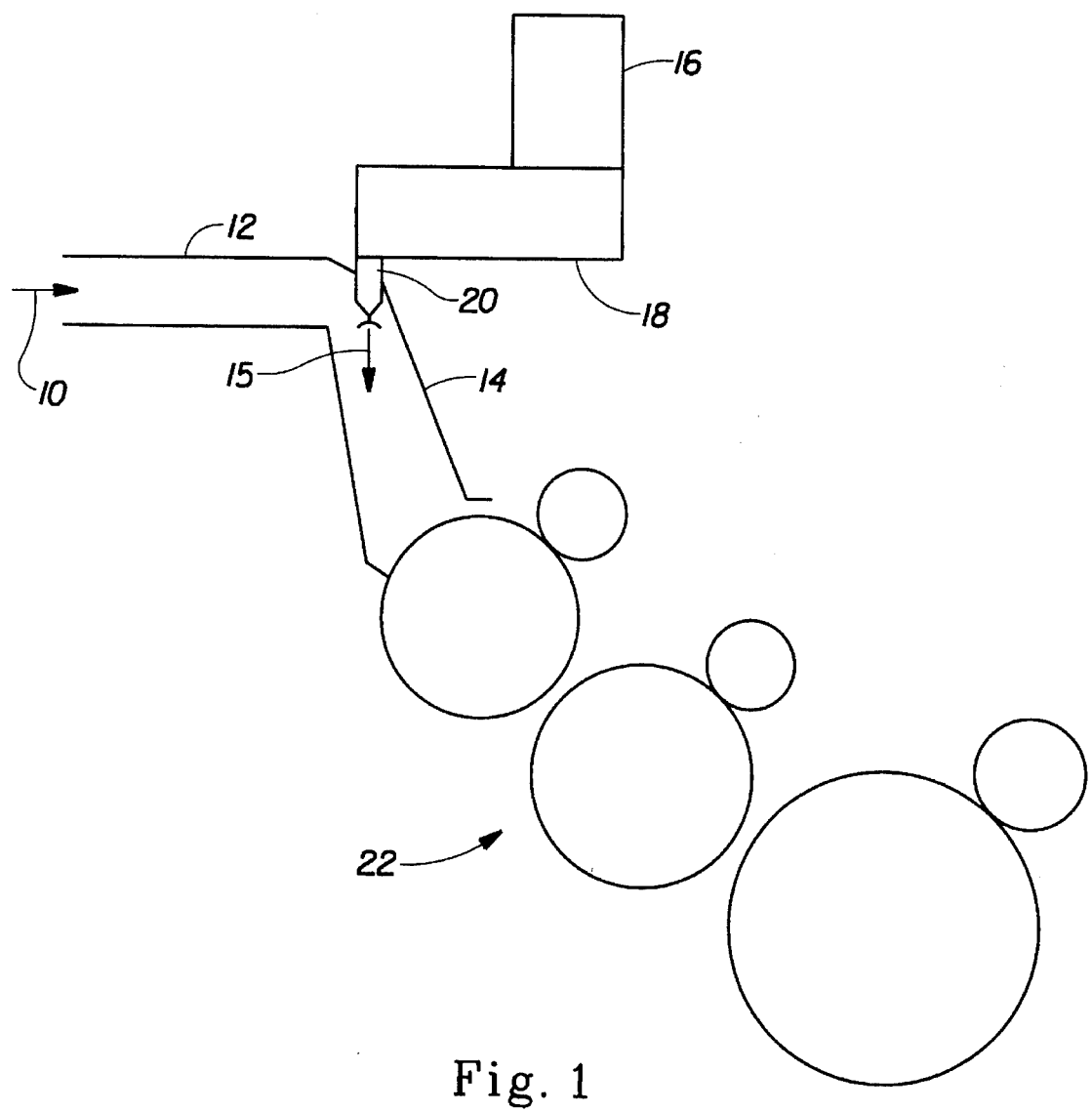
FIG. 1 is a schematic diagram of an apparatus for preparing a homogeneous admixture of carded staple fibers and melt blown fibers.

Typical apparatus for preparing melt blown fiber based web structures are schematically illustrated in FIG. 1 of U.S. Pat. No. 4,773,903, incorporated herein by reference. As described in U.S. Pat. No. 4,773,903, this apparatus includes a die which has an extrusion chamber through which liquified microfiber-forming material is advanced; die orifices, arranged in line across the forward end of the die and through which the microfiber-forming material is extruded; and cooperating gas orifices through which a gas, typically heated air, is forced at very high velocity. The high-velocity gaseous stream draws out and attenuates the extruded microfiber-forming material, whereupon the microfiber-forming material solidifies as microfibers during travel to a collector. The collector is typically a finely perforated screen, which is depicted in U.S. Pat. No. 4,773,903 in the form of a closed loop belt, but which can take alternative forms such as a flat screen or a drum or cylinder. A gas-withdrawal apparatus may be positioned behind the collector to assist in deposition of the fibers and removal of the gas. One collector may service more than one melt blowing die.

A web of melt blown fibers is readily disintegrated into fibers, e.g., using a picker, or, in some cases, a bale opener, or opener.

We turn now to the 1.2 to 5 denier staple synthetic fibers. Typically, these have lengths ranging from ½ to 1½ inches (about 1.25 to 3.8 cm); a typical good average is ¾ inch (about 1.9 cm).

The staple synthetic fibers can be non-elastic or elastic. Non-elastic 1.2 to 5 denier staple synthetic fibers can be prepared from synthetics, e.g., polyolefins such as polypropylene and polyethylene, polyesters such as polybutylene terephthalate and polyethylene terephthalate, copolyesters, polyamides such as nylon, polyacrylics, and blends of these. Preferably these are bicomponent fibers having a sheath of one polymer surrounding a core of a second polymer wherein the sheath polymer has a lower melting point than the core polymer. Preferred bicomponent fibers have sheath/core combinations of polyethylene/polypropylene, polyethylene/polyester, polypropylene/polyester, and copolyester/polyester. Specific examples of such fibers are 1.7 and 3 denier polyethylene/polyester sheath core fibers available from BASF Corporation as Products 1051 and 1050, respectively; 2 and 3 denier copolyester/polyester sheet/core fibers available from Celanese Fibers as Type 354; and 1.5 and 3 denier polyethylene/polypropylene sheath/core fibers available from Chori America as Daiwabo NBF Type H.

Preferably, the staple synthetic fibers are carded fibers. Carded fiber webs are readily disintegrated into carded fibers, e.g., using a picker, or in some cases, a bale opener or opener.

The staple synthetic fibers can also be obtained from spun-bonded webs. Spun bonded webs are produced by extruding continuous filaments, e.g., by extruding a thermoplastic polymer from an extruder through linear die heads, with circular or other configuration openings, vertically downwardly through ambient air to solidify the molten fibers; drawing the fibers, e.g., in a high velocity air stream or by passing them through independently driven draw roll sets, to reduce each filament to textile denier; delivering the drawn fibers, preferably using an air aspirator or other forwarding device, onto a preferably continuous porous collection or forming surface; passing, for example, across a vacuum box in a forming section to form an unbonded web; and bonding, e.g., by applying heat and pressure to plasticize the fibers in the web and render them cohesive, e.g., in a heat bonding nip in a forming section to produce an autogeneously bonded web, by exposure to chemicals which plasticize the fibers and render them cohesive, by needle punching, by hydroentangling, or by applying adhesives. A preferred sequence of processing steps is described at columns 5 and 19 of Sisson U.S. Pat. No. 4,107,364, incorporated herein by reference. Spun bonded webs are readily disintegrated into fibers, e.g., using a picker or in some cases a bale opener or opener.

Elastic properties can be imparted to the staple synthetic fibers by crimping, e.g., as described in Hauser, U.S. Pat. No. 4,118,531, incorporated herein by reference. Other methods of providing elastic staple synthetic fibers include using elastic resins such as Kraton based resins, metalocence polyethylene resins, urethane resins and other stretch chemistries familiar to the art.

Preferred staple synthetic fibers herein are non-elastic bicomponent fibers.

The homogeneous admixture of melt blown fibers and staple synthetic fibers can be formed, for example, by merging air conveyed streams of the fibers, preferably using turbulent flow (e. g., using air streams in cross directions or utilizing fins to transform laminar flow to turbulent flow), or by forming melt blown fibers into a stream of staple fibers. The homogeneous admixture is readily formed into a web, e.g., by air laying. For example, an air conveyed stream of melt blown fibers from disintegrating a melt blown fiber web using a picker and an air conveyed stream of carded fibers from disintegrating a carded fiber web using a picker are metered into each other and the merged stream is air laid to form a web. In another example, as depicted in FIG. 1, a melt blowing unit is built into a standard carding unit, to produce a web of an admixture of melt blown fibers and carded staple fibers. With reference to FIG. 1, a staple fiber stream 10 is air conveyed via a duct 12 into a carding unit inlet duct 14, and resin is fed via a hopper 16 and an auger 18 through melt blowing nozzles 20 which form melt blown fibers as represented by arrow 15 at the inlet to duct 14 where the melt blown fibers merge with the staple fiber stream 10 and the formed admixture is fed via duct 14 to carding rolls 22.

We turn now to the hydroentangling. The term "hydroentangling" is used herein to refer generally to subjecting a web of fibers to high velocity water jets (or jets of other fluid) to cause fiber entanglement to interlock the fibers and produce a nonwoven fabric. The hydroentangling process may also function to create apertures in the fabric.

Suitable hydroentangling processes for use herein are described in Evans U.S. Pat. No. 3,485,706, incorporated herein by reference. As indicated in U.S. Pat. No. 3,485,706, hydroentangling apparatus includes a series of orifice manifolds directed at an apertured supporting surface. The apertured supporting surface can be, for example, a wire or screen, a perforated plate, or a perforated drum. The orifice size in the orifice manifold generally ranges from 0.003 to 0.03 inches (0.0076 cm to 0.076 cm), the orifice spacing generally ranges from 0.01 to 0.1 inch (0.025 cm to 0.25 cm), the water pressure (i.e., the pressure in a manifold) generally ranges from 200 to 5000 psi (9,576 N/m$^2$ to 239,400 N/m$^2$), the web to orifice separation generally ranges from 0 to 6 inches (0 to 15.25 cm), the number of passes of the web through the hydroentangling apparatus generally ranges from 1 to 100, the aperture size in the apertured supporting surface generally ranges from 0.01 to 0.25 inch (0.025 cm to 0.64 cm), (diameter or equivalent), and the proportion of open area in the apertured supporting surface generally ranges from 10 to 98%. The apertures in the supporting surface typically are spaced at regular intervals symmetrically over the whole surface. Suitable supporting surfaces are described in Widen, "Forming Wires for Hydroentanglement System," Nonwoven's Industry, 11/88, pp. 39–43, incorporated herein by reference. In a preferred process, manifolds are used with 0.005 inch (0.0127 cm) diameter orifices spaced on 0.025 inch (0.064 cm) centers with spacing between the orifice outlets and the web being treated ranging from ¼ inch to ¾ inch (0.64 cm to 1.9 cm).

Forming apertures in the web in the hydroentangling process, i.e., simultaneously with hydroentangling, can be carried out as described in Example 41 of the above referenced U.S. Pat. No. 3,485,706 to Evans.

Forming apertures in the web in the hydroentangling process simultaneously with hydroentangling, is also carried out using a supporting roll as described in conjunction with FIG. 7 of Suzuki et al., U.S. Pat. No. 4,704,112, which has a series of projections to distribute the fibers aside under the pressure of the water jets and a plurality of perforations (e.g., 0.2 to 1.0 mm diameter) for drainage. This patent is incorporated herein by reference.

Aperturing can be fostered by using a supporting surface consisting of a wire made up of warp and fill filaments and knuckles of accentuated height where the warp and fill filaments cross, so that deflection of the water at the knuckles will force the fibers away from such to produce apertures.

Apertures that are round, square, oval, rectangular or of other configuration, aligned, e.g., in the machine and/or cross machine direction, can be obtained.

As indicated above, effective apertures have open area preferably occupying 8 to 40%, very preferably 12 to 25%, of the exposed surface area of the fabric which is formed.

After the hydroentangling step, the resulting fabric can be dried by web drying methods well known in the nonwoven and paper manufacturing arts, such as conveying the web, preferably on a felt, around the surface of hot cans to evaporate the water in the fabric, or by infrared heating or through-air drying.

If desired, additional tensile strength can be imparted to the dried fabric by causing bonding of fibers to one another, e.g., by thermally bonding by heating the fabric so fibers bond at contact points, or via thermal embossing rolls in a hot calendering process to obtain a desired caliper and impart a patterned imprint such as described below, or by any other method causing interfiber bonding.

The topsheet is preferably constituted only of the nonwoven fabric prepared by forming a web comprising a homogeneous admixture of from 1 to 50% by weight of melt blown fibers and from 99 to 50% by weight of 1.2 to 5 denier staple synthetic fibers and hydroentangling as described above.

Less preferably, the topsheet can be a composite structure made up from a composite web prepared by forming a batt constituted of nonwoven fabric as described above which is hydroentangled to another batt or batts (e.g., prepared only from 1.2 to 5 denier staple synthetic fibers). Hydroentangling of the batts together is readily carried out as described in Austin et al., U.S. Pat. No. 5,144,729, by, e.g., using a tightly woven screen (more tightly woven than 50 mesh) or a smooth surface with apertures smaller than 0.02 inch (0.05 cm) in diameter. This patent is incorporated herein by reference.

The resultant fabric or composite may be subjected to calendering to adjust the caliper, e.g., using a cold calender equipped with smooth rolls to provide a smooth soft surface feel or a hot calender equipped with patterned rolls to impart a patterned imprint. A topsheet typically has a caliper ranging from 6 to 20 mils (152 microns to 508 microns), preferably from 8 to 16 mils (203 microns to 406 microns).

A topsheet is readily obtained from a continuous web of the fabric or composite, for example, by die cutting to the appropriate configuration. Typically the topsheet or portion thereof of the present invention, i.e., prepared by forming a web comprising a homogeneous admixture of melt blown fibers and staple synthetic fibers and hydroentangling to form a fabric as described above, is characterized by a rewet value ranging from 0.1 to 0.5 grams; an opacity of land areas of the exposed surface (the surface that will face the body when the topsheet is in use in a disposable absorbent article) denoted by a gray level of at least 115, preferably greater than 120, more preferably greater than 125; a machine direction tensile strength in a cold calendered fabric ranging from 500 to 800 grams/inch (197 g/cm to 315 g/cm); a cross machine direction tensile strength in a cold calendered fabric ranging from 150 to 200 g/in (59 g/cm to 79 g/cm); a machine direction tensile strength in a thermally bonded fabric greater than 800 g/in (315 g/cm); and a cross machine direction tensile strength in a thermally bonded fabric greater than 300 g/in (118 g/cm).

Figure 2:
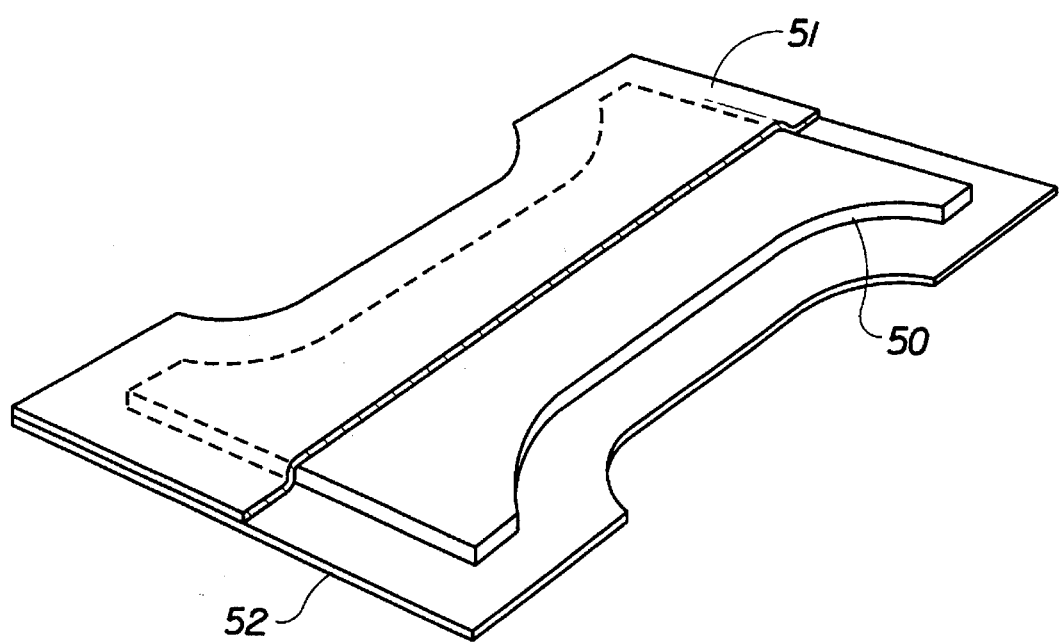
FIG. 2 is a perspective view of a disposable diaper of one embodiment of the invention.

As indicated above, a disposable absorbent article herein comprises a liquid pervious topsheet (as described above), a liquid impervious backsheet and an absorbent core positioned between the topsheet and the backsheet. This combination of elements is illustrated in FIG. 2 for a preferred embodiment of an hourglass configuration disposable diaper wherein such diaper includes an absorbent core 50, a topsheet 51 (partially broken away to depict the core 50) and a liquid impervious backsheet 52.

The backsheet for a disposable absorbent article herein can be constructed, for example, from a thin, plastic film of polyethylene, polypropylene, or other flexible moisture impeding material which is substantially water impervious. Polyethylene, having an embossed caliper of approximately 1.5 mils (38 microns), is especially preferred.

The absorbent core for a disposable absorbent article herein may assume a wide variety of sizes and shapes, such as rectangular or hourglass shapes. The absorbent core may be made from a variety of commonly used materials such as comminuted wood pulp, typically referred to as airfelt. The absorbent core may further contain absorbent gelling materials.

The absorbent core is superimposed on the backsheet and is preferably joined thereto by means known in the art, e.g., adhesive bonding, preferably with longitudinally oriented adhesive bonds. The topsheet is positioned on top of the absorbent core with or without intervening layer(s) and is typically, at least partially peripherally bonded to the backsheet, e.g., using hot melt adhesive beads, ultrasonic means or thermomechanical means where pressure causes adjoining surfaces to melt together.

The following specific examples illustrate the practice of the present invention but are not intended to be limiting thereof.

EXAMPLE I

A topsheet is prepared as follows:

A melt blown polybutylene terephthalate microfiber web (23 grams per square yard (27.5 g/m$^2$)) is disintegrated using a picker to produce fibers of average denier of about 0.2 and average length of about 1 min.

Carded polybutylene terephthalate fibers of average denier of about 1.7 and average length of about ¾ inch (1.9 cm) are used as the staple fiber component.

A homogeneous admixture of 0.28 g of the melt blown fibers and 2.50 g of the staple fibers is formed by merging air conveyed streams of the fibers and depositing the resulting admixture on a 1 foot (30.5 cm) square 100 mesh wire screen with a vacuum being pulled on the rear side of the screen (i.e., the side opposite from that on which depositing is being carried out).

The formed body is transferred to a 13×20 hydroentangling wire (13 wires by 20 wires per inch (5.1 by 7.9 wires/cm)). For the hydroentangling nozzles, manifolds are used with 0.005 inch (0.013 cm) diameter orifices spaced on 0.025 inch (0.064 cm) centers with spacing between the orifice outlets and the body being treated being about ½ inch (1.27 cm). Two passes are carried out at a water pressure of 200 psi (9,576 N/m$^2$), followed by 2 passes at a water pressure of 1200 psi (57,456 N/m$^2$) followed by two passes at a water pressure of 1600 psi (76,600 N/m$^2$). An apertured web is formed.

The apertured web is dried by application of a stream of 150° F. (65.5° C.) air (air through drying) for 30 minutes.

Cold calendering is then carried out to adjust the caliper to about 14 mils (356 microns).

The formed fabric has a basis weight of 25 grams/square yard (29.9 g/m$^2$), effective apertures having open area occupying about 20% of the exposed surface area of the fabric, a rewet value of 0.5 g, opacity denoted by a gray level of about 130, a soft to the touch feel, a machine direction tensile strength of about 700 g/in (276 g/cm) and a cross machine tensile strength of about 175 g/in (69 g/cm).

When thermal bonding is utilized after drying (air through process using 300° F. (149° C.) air for 5 minutes), the machine direction tensile strength is about 1000 g/in (394 g/cm) and the cross machine tensile strength is about 400 g/in (157 g/cm).

When the above process is modified so that the melt blown fibers are merged with a stream of staple fibers entering a carding unit, or so that the staple fibers are 3 denier flat crimped polyethylene/polyester sheath/core bicomponent fiber, e.g., product 1050 from BASF Corp., similar basis weight, apeturing, rewet values, opacity, and tensile strengths are obtained.

EXAMPLE II

A disposable diaper is prepared structured as depicted in FIG. 2 with the topsheet being prepared by die cutting the depicted configuration from fabric prepared as described in Example 1. The absorbent core is air-laid wood pulp. The backsheet is polyethylene having an embossed caliper of about 1.5 mils (38 microns).

While particular embodiments of the present invention have been illustrated and described, it will be obvious to those skilled in the art that various other changes and modifications can be made without departing from the spirit and scope of the invention. It is therefore intended to cover in the appended claims all such changes and modifications that are within the scope of this invention.

What is claimed is:

1. A liquid pervious topsheet for a disposable absorbent article, having a basis weight ranging from 10 to 40 g/yd$^2$ and consisting of an apertured body with at least the upper portion thereof comprising nonwoven fabric prepared by forming a web comprising a homogeneous admixture of from 1 to 50% by weight of melt blown fibers and from 99 to 50% by weight of 1.2 to 5 denier staple synthetic fibers and hydroentangling the fibers to form a fabric and to form effective apertures through the thickness of the fabric.

2. The topsheet of claim 1 wherein the effective apertures have an open area occupying 8 to 40% of the exposed surface area of the fabric.

3. The topsheet of claim 2 wherein the effective apertures have an open area occupying 12 to 25% of the exposed surface area of the fabric.

4. The topsheet of claim 1 wherein the staple synthetic fibers are carded fibers.

5. The topsheet of claim 1 wherein the effective apertures have an open area occupying 8 to 40% of the exposed surface area of the fabric and the staple synthetic fibers are carded fibers.

6. The topsheet of claim 1 which has a basis weight ranging from 15 to 30 g/yd$^2$.

7. The topsheet of claim 1 wherein the melt blown fibers are non-elastic polyester fibers.

8. The topsheet of claim 1 which has a basis weight ranging from 15 to 30 g/yd$^2$, wherein the effective apertures have an open area occupying 8 to 40% of the exposed surface area of the fabric, wherein the staple synthetic fibers are carded fibers and wherein the melt blown fibers are non-elastic polyester fibers.

9. A disposable absorbent article comprising a liquid pervious topsheet, a liquid impervious backsheet and an absorbent core positioned between said topsheet and said backsheet, said liquid pervious topsheet having a basis weight ranging from 10 to 40 g/yd$^2$, having an apertured body and having at least the upper portion thereof comprising nonwoven fabric prepared by forming a web comprising a homogeneous admixture of from 1 to 50% by weight of melt blown fibers and from 99 to 50% by weight of 1.2 to 5 denier staple synthetic fibers and hydroentangling the fibers to form a fabric and to form effective apertures through the thickness of the fabric.

10. The topsheet of claim 1 wherein said hydroentangling is performed on an apertured supporting surface having fewer than 20 wires per inch in at least one direction and having no more than about 20 wires per inch in either direction.

11. The disposable absorbent article of claim 9 wherein said hydroentangling is performed on an apertured supporting surface having fewer than 20 wires per inch in at least one direction and having no more than about 20 wires per inch in either direction.

\* \* \* \* \*